United States Patent
Siebold (10) Patent No.: US 9,811,609 B2
(45) Date of Patent: Nov. 7, 2017

(54) DEVICE FOR PLACING BORE CHANNELS WHEN ATTACHING ARTIFICIAL LIGAMENTS TO THE BONE AND METHOD FOR PRODUCING A CORRESPONDING DEVICE

(71) Applicant: Rainer Siebold, Walldorf (DE)

(72) Inventor: Rainer Siebold, Walldorf (DE)

( * ) Notice: Subject to any disclaimer, the term of this patent is extended or adjusted under 35 U.S.C. 154(b) by 594 days.

(21) Appl. No.: 14/359,823

(22) PCT Filed: Nov. 21, 2012

(86) PCT No.: PCT/DE2012/200076
§ 371 (c)(1),
(2) Date: May 21, 2014

(87) PCT Pub. No.: WO2013/075711
PCT Pub. Date: May 30, 2013

(65) Prior Publication Data
US 2014/0324060 A1 Oct. 30, 2014

(30) Foreign Application Priority Data

Nov. 21, 2011 (DE) .......................... 10 2011 086 717

(51) Int. Cl.
*A61B 17/17* (2006.01)
*G06F 17/50* (2006.01)
*A61B 17/56* (2006.01)

(52) U.S. Cl.
CPC .......... *G06F 17/50* (2013.01); *A61B 17/1714* (2013.01); *A61B 17/1764* (2013.01); *A61B 2017/568* (2013.01)

(58) Field of Classification Search
CPC .................. A61B 17/1764; A61B 17/1714
See application file for complete search history.

(56) References Cited

U.S. PATENT DOCUMENTS 5,735,277 A * 4/1998 Schuster ............. A61F 2/30942
600/407
6,126,690 A * 10/2000 Ateshian ............... A61F 2/4241
623/22.4
(Continued)

FOREIGN PATENT DOCUMENTS

DE 3339259 C1 3/1985
WO WO 2011/029911 A1 3/2011

OTHER PUBLICATIONS

The International Bureau of WIPO, Advance E-Mail of the International Preliminary Report on Patentability (English translation of the ISA's Written Opinion) for International Application No. PCT/DE2012/200076, dated Jun. 5, 2014, 7 pages, Switzerland.
(Continued)

*Primary Examiner* — Zade Coley
(74) *Attorney, Agent, or Firm* — Alston & Bird LLP (57) ABSTRACT

A device for the patient-specific, individual anatomic placement of bore channels when attaching artificial ligaments to bones, namely for use in placing boreholes on the thigh and lower leg during anterior cruciate ligament reconstruction, is provided with a probe (1) to be introduced into a joint via an arthroscopy portal and with a targeting head (2) disposed on the distal end of the probe. The targeting head (2) comprises a targeting template (3) which is produced individually using a 3-D imaging method, in particular 3-D magnetic resonance tomography (3-D-MRT) or 3-D computer tomography (3-D-CT), and which is a negative imprint of the osseous surface relief in the region where the torn ligament attaches to the bone in question, in particular where the cruciate ligament attaches to the thigh or lower leg. The targeting template (3) comprises at least one passage (4) for marking the bore channel that is to be produced on the bone, and a hand grip (7) is provided on the proximal end of the
(Continued)

probe (1) for holding and positioning. The invention also relates to a method for producing a corresponding device.

10 Claims, 3 Drawing Sheets

(56) References Cited

U.S. PATENT DOCUMENTS

| | | | | |
|---|---|---|---|---|
| 6,459,948 B1* | 10/2002 | Ateshian | ............ | A61F 2/30942 623/11.11 |
| 6,510,334 B1* | 1/2003 | Schuster | ............ | A61F 2/30942 128/920 |
| 6,551,258 B1* | 4/2003 | Herling | ............ | A61B 5/103 600/595 |
| 8,282,646 B2* | 10/2012 | Schoenefeld | ........ | A61B 17/154 606/88 |
| 8,500,740 B2* | 8/2013 | Bojarski | ............ | A61B 17/1764 606/86 R |
| 9,308,053 B2* | 4/2016 | Bojarski | ............ | A61B 17/1764 |
| 2007/0233141 A1* | 10/2007 | Park | ............ | A61B 17/155 606/88 |
| 2007/0288030 A1* | 12/2007 | Metzger | ............ | A61B 17/154 606/87 |
| 2010/0076563 A1* | 3/2010 | Otto | ............ | A61B 5/103 623/20.14 |
| 2010/0298894 A1* | 11/2010 | Bojarski | ............ | A61B 17/1714 606/86 R |
| 2011/0029093 A1* | 2/2011 | Bojarski | ............ | A61F 2/389 623/20.35 |
| 2011/0313478 A1* | 12/2011 | Herdrich | ............ | A61B 17/1764 606/86 R |
| 2012/0041446 A1* | 2/2012 | Wong | ............ | A61B 17/1703 606/96 |
| 2012/0209394 A1* | 8/2012 | Bojarski | ............ | A61F 2/30942 623/20.32 |
| 2013/0085500 A1* | 4/2013 | Meridew | ............ | A61B 17/15 606/89 |

OTHER PUBLICATIONS

International Searching Authority, International Search Report (ISR) and Written Opinion for International Application No. PCT/DE2012/200076, dated Apr. 8, 2013, 10 pages, European Patent Office.

* cited by examiner

DEVICE FOR PLACING BORE CHANNELS WHEN ATTACHING ARTIFICIAL LIGAMENTS TO THE BONE AND METHOD FOR PRODUCING A CORRESPONDING DEVICE

CROSS REFERENCE TO RELATED APPLICATIONS

This application is a national stage application, filed under 35 U.S.C. §371, of International Application No. PCT/DE2012/200076, filed Nov. 21, 2012, which claims priority to German Application No. 10 2011 086 717.1, filed Nov. 21, 2011, both of which are hereby incorporated by reference in their entirety.

BACKGROUND

The invention relates to a device for the patient-specific, individual anatomic placement of bore canals when attaching artificial ligaments on bones, in particular for use when placing bore canals on the thigh and lower leg during anterior cruciate ligament reconstruction. Furthermore, the invention relates to a method for the manufacture of a corresponding device.

The invention basically relates to a customized instrument for the patient-specific, individual anatomic placement of bore canals on human or animal bones to attach artificial ligaments. To make the explanation of the teaching according to the invention easier to understand, the cruciate ligament reconstruction is exemplified below, namely in representation of any patient-specific, individual anatomic placement of bore canals for ligament reconstruction.

Holes are drilled on the thigh and lower leg during cruciate ligament reconstruction, for the secure anchorage of artificial cruciate ligaments. The anatomical positioning of the bore canals on the thigh and lower leg (femur and tibia) during anterior cruciate ligament reconstruction is of vital importance for the proper biomechanical post-operative function of the knee. For lack of a sufficiently sound cruciate ligament targeting instrument, malpositioning, specifically malpositioning in excess of more than one centimeter, of the bore canal or bore canals during the surgery is not uncommon. Said malpositioning either results in permanent mobility impairments of the patient, usually associated with pain. In addition, said malpositioning is frequently the reason for "wearing out" of the cruciate ligament reconstruction. This is associated with the risk of instability of the reconstruction and inevitable failure after some time. Complex and expensive revision surgeries are often required, with their outcome always being worse than the one of a properly performed initial surgery with the accurate placement of the bore canals.

The sound knowledge of the anatomy of the joints, in particular the anatomy of the attachment point of the cruciate ligament on the thigh and lower leg as well as the knowledge of different osseous reference points on the thigh and lower leg are the prerequisite for the correct placement of the bore canals. Only then can the commercially available bore canal targeting devices known from the practice, which are usually equipped with a punctiform sharpened targeting arm, be placed in anatomically accurate fashion. The disadvantage of all targeting devices known from the practice is that not only do they require the anatomical know-how and an accurate placement of the targeting device, but they do in fact have a uniform shape, such that the optimal placement of the bore canals is already impossible insofar—for lack of an individual shape of the targeting device. Consequently, errors are inevitable, in particular based on the fact that the majority of cruciate ligament reconstruction surgeries are performed by surgeons who are only treating a small number of torn cruciate ligaments each year.

BRIEF SUMMARY

Therefore, the object of the present invention is to design and upgrade the device for the placement of bore canals during ligament reconstruction, in particular cruciate ligament reconstruction known from the practice such as to facilitate an optimal positioning of the bore canal on the bones to be connected with the artificial ligaments. When optimally adjusted to the actual conditions, the device should be easy to handle. Furthermore, a method for the manufacture of a corresponding device is to be disclosed.

The object mentioned above is solved with the characteristics of the independent patent claims. Accordingly, the device according to the invention comprises the following characteristics:

The device according to the invention is equipped with a probe to be inserted into a joint through an arthroscopy portal. A targeting head is provided at the distal end of the probe. The targeting head comprises a targeting template, which has been produced individually using a 3D imaging method, in particular 3D magnetic resonance tomography or 3D computed tomography. Specifically, the targeting template is a negative imprint of the osseous surface contour in the region where the torn ligament attaches to the respective bone, in particular where the cruciate ligament attaches to the thigh or lower leg.

In other words, the device according to the invention is a customized anterior cruciate ligament targeting instrument for the patient-specific, individual anatomic placement of bore canals on the thigh and lower leg based on a 3D magnetic resonance image or a 3D computed tomography scan conducted before the surgery.

The targeting template comprises at least one passage for marking the bore canal to be produced on the bone, namely for the so-called single bundle technique. For the realization of the double bundle technique, the targeting template comprises two passages for marking two bore canals on the bone. From a design point of view, a handle grip for positioning is provided at the proximal end of the probe, such that a hand-held targeting device with an individual targeting head or with an individual targeting template is created in the fashion according to the invention.

As stated in certain of the claims, the method according to the invention comprises the following procedure steps:

Conduct of a 3D MRI or a 3D CT scan of the inured joint and optionally the healthy joint, in particular the knee, to obtain 3D data;

Generation of a 3D computer model of the injured joint having the respective surface profile, in particular the respective surface profile of the individual attachment point of the cruciate ligament on the thigh and lower leg, using suitable software;

Creation of individual targeting templates, targeting heads and/or targeting devices.

The invention is based on the latest know-how used in cruciate ligament surgery, according to which a size-adapted, "customized" anterior cruciate ligament replacement is to be realized. In so doing, the major size differences between knee joints should be accounted for. Accordingly, smaller knee joints have a smaller attachment point of the cruciate ligament and vice versa. The size of the knee does not necessarily correlate with the size of a person. In any case, corresponding size differences between knees are currently not individually considered during the surgery. Said individual consideration can artfully be achieved on the basis of the device according to the invention, manufactured as stated in the method according to the invention.

While the cruciate ligament targeting devices for the creation of the bore canals on the thigh and shinbone as they are known from the practice fail to deliver distinct assistance with the placement of the bore canals and in addition fail to account for the individual size of the cruciate ligament insertion on the thigh and on the shinbone, the device according to the invention provides a customized cruciate ligament targeting instrument, which enables an individual reconstruction of the cruciate ligament.

The individually manufactured targeting template and optionally the entire targeting head including the targeting template can be exchanged on the instrument in an advantageous fashion.

According to certain of the independent claims, the probe with the targeting head and the targeting template is part of a fixation device for attaching the probe in the region of the cruciate ligament or can be combined with a corresponding fixation device. Said type of targeting device is inserted with the probe into the joint, for example through an arthroscopy portal, whereby part of the targeting device located outside the joint is applied and positioned accurately fitting for example on the shinbone.

At this point, it should be noted that the invention utilizes the individual adjustment of a targeting template or a targeting head, irrespective of the specific device and irrespective of the specific technique that is used. The individualization of the targeting template is relevant to account for the anatomical conditions.

The fixation device comprises at least one guide sleeve for defining the drill hole location and/or the drilling angle and/or the drilling diameter and/or for guiding wires, etc., namely for the purpose of the reconstruction. An optimal surgical instrument is thus created.

In light of the explanations provided above, it becomes clear that the device according to the invention makes it possible to provide two individually manufactured targeting templates and targeting devices for each patient, namely one each for the thigh and the lower leg. The production is based on a 3D magnetic resonance image or a 3D computed tomography image, whereby it is essentially possible to use any types of imaging methods. The device according to the invention helps ensure the correct individual anatomical placement of the bore canals on the thigh and lower leg during cruciate ligament reconstruction.

Taking into account the size of the attachment point of the cruciate ligament on the thigh and lower leg, an ideal size of the bore canals can be specified with the use of a so-called insertion table. The device according to the invention can then be manufactured for both the single bundle technique with one bore canal as well as for the double bundle technique with two bore canals, such that the reconstruction of the individual length/surface area of the attachment point of the cruciate ligament on the thigh and lower leg is ensured individually for each patient.

The device according to the invention with the individual targeting template is manufactured on the basis of the 3D magnetic resonance tomography or the 3D computed tomography image of the injured knee and—in a further advantageous fashion—also of the healthy knee, to allow a comparative optimization.

Suitable software is used to "produce" a digital 3D model of the injured knee in the computer model or to simulate a 3D model. Said model visualizes the osseous surface profile and the attachment points of the torn cruciate ligament on the thigh and lower leg. A 3D model of the healthy knee can be produced to illustrate the stumps of the cruciate ligaments, to facilitate a comparison for optimization purposes.

Two digital targeting templates for the thigh and lower leg can be produced based on the computer model, to help equip an individual targeting device accordingly. The targeting templates are ultimately negative imprints of the actual surface profile and accurately fit on the individual surface contour of the respective patient in the area of the attachment point of the cruciate ligament on the thigh and lower leg.

In addition, it is conceivable to use the individually designed targeting templates or targeting devices to conduct a simulation on the 3D computer model by means of suitable software, such that it is possible to review the digital templates on the complete targeting device prior to the actual manufacture of the targeting templates. In a particularly advantageous fashion, said controls can be conducted by the future surgeon by means of the 3D model, such as to allow him to review the function resulting from the optimization. Furthermore, the surgeon has the option of making corrections to the 3D model, namely to realize a further optimization.

In addition, it is conceivable that the localization of the bore canals, the drilling angles, the size of the bore canals as well as the technique to be conducted (single bundle or double bundle) are defined interactively, to the extent possible on the basis of data retrievable from a file, for example on the basis of data contained in an insertion table. Manual data input is likewise an option.

Following the optimization, the patient-specific targeting templates and optionally targeting devices for thighs and lower legs are manufactured on the basis of the optimized 3D model, preferably of metal or synthetic material. Any shape-giving methods can be used, wherein the manufacture is based on the optimized 3D data.

The targeting devices manufactured in this fashion can be placed accurately fitting onto the respective patient's osseous surface contour and adjusted there. During the surgery, the drills are applied by means of integrated guide sleeves for the creation of the bore canals or the Kirschner wires are threaded through the bore canals for the performance. Only then are the targeting devices removed from the thigh and lower leg.

It is basically conceivable that the individually manufactured targeting template or the individually manufactured targeting head can be mounted on commercially available targeting devices, wherein the targeting devices known from the practice for placement on the lower leg can consist of two parts and the targeting devices for the thigh can regularly consist of only one part.

The targeting template according to the invention and a complete targeting device are used in surgeries as follows:

The individual tibial targeting template (for the thigh) is mounted accurately fitting onto the osseous surface contour through an arthroscopy portal under arthroscopic view and adjusted there. The targeting template is retained from the outside with a grab handle. Then, the spaces of the bore holes can be used to mark the bore canals. Next, the templates are removed from the joint and holes are drilled in common fashion at the marked locations.

The individual tibial targeting device is likewise inserted into the joint through an arthroscopy portal. It is adjusted to the osseous surface profile of the lower leg in the region of the cruciate ligament under arthroscopic view. The part of the tibial targeting device located outside the joint is placed accurately fitting onto the shinbone. As a result, the drilling angle on the tibial head is defined quasi automatically. Based on the design of the targeting device, the desired bore canal diameter with the corresponding defined angle is drilled using either the traditional single bundle technique or the double bundle technique, on the basis of the guide sleeves assigned to the targeting head. Kirschner wires can then be inserted. Essentially, the specific technique is irrelevant, according to which either a single bore canal or two bore canals are produced.

The device according to the invention or the individually produced targeting device can likewise be used on the lower leg, both within the scope of a hand-held instrument as well as within the scope of a targeting device to be mounted from the outside.

The individual femoral targeting template (for the thigh) is placed accurately fitting onto the osseous surface contour through an arthroscopy portal under arthroscopic view and adjusted there. It is retained from the outside with a grab handle. The spaces of the bore holes can then be used for marking the bore canals. Next, the templates are removed from the joint and holes drilled in the common fashion at the marked locations.

The individual femoral targeting device is inserted into the femoral region of the cruciate ligament with the patient-specific imprint of the surface structure, i.e., with the patient-specific template, namely through an anteromedial or anterolateral arthroscopy portal. The instrument is put onto the osseous structures of the region of the cruciate ligament with its accurately fitting 3D imprint on the thigh in the region of the lateral wall of the intercondylar notch under arthroscopic view. In this case, the holes are drilled through an anteromedial portal.

Alternatively, the instrument or the targeting arm can be inserted through the anterolateral portal. So-called outside-in drilling from the lateral thigh is possible.

Based on the individual design of the targeting device, the holes are drilled analogous to one or two guide sleeves for the realization of the single bundle technique or the double bundle technique with a defined diameter of the bore canals. Kirschner wires can be inserted through the bore hole(s).

After the creation of the bore canals, the transplant is inserted and fastened in a traditional fashion, namely on the basis of an individual creation of the bore canals and in consideration of the patient-specific conditions.

BRIEF DESCRIPTION OF THE FIGURES

At this point, there are various options for embodying and implementing the teaching of the present invention in an advantageous manner. For this purpose, reference is hereby made on the one hand to the claims dependent on claims 1, 2 and 4 and on the other hand to the following explanation of preferred exemplary embodiments of the invention by means of the drawing. Generally preferred embodiments and upgrades of the teaching are also explained in connection with the explanation of the preferred exemplary embodiments by means of the drawing. In the drawing:

DETAILED DESCRIPTION OF VARIOUS EMBODIMENTS

Figure 1:
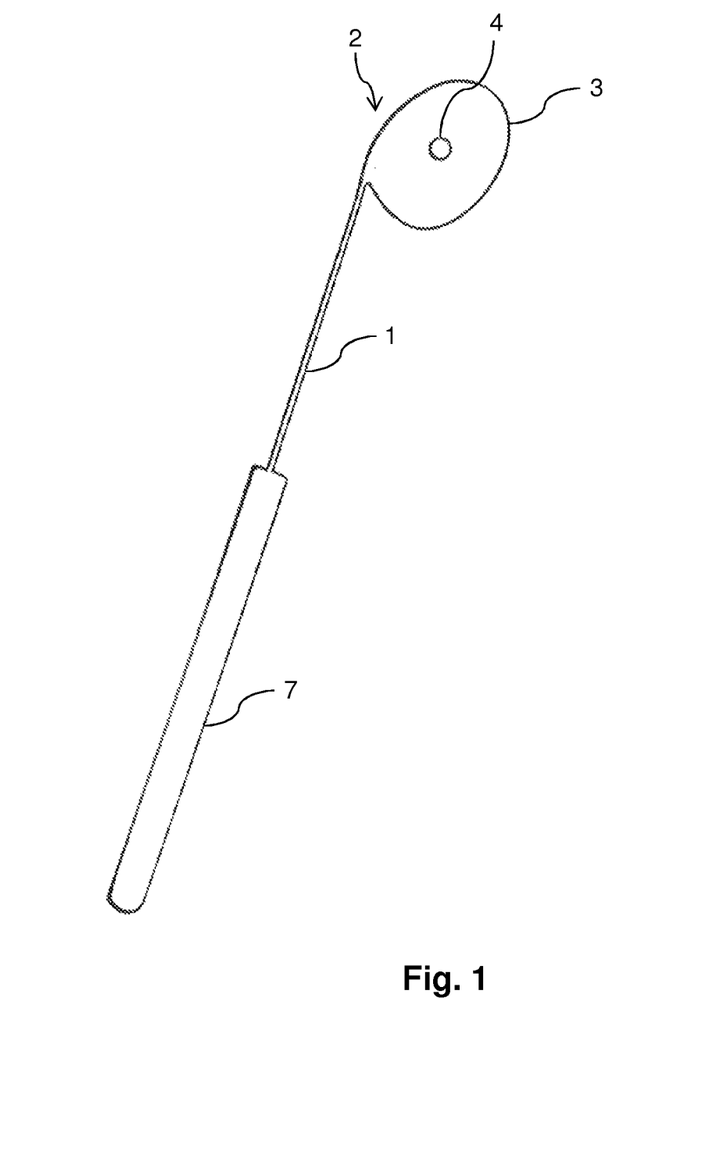
FIGS. 1 and 2 show schematic representations of two exemplary embodiments of a device according to the invention, using as an example a hand-held device with a grab handle, probe and targeting head, comprising an individual targeting template, for use of the single bundle technique on the one hand (FIG. 1) and of the double bundle technique on the other hand (FIG. 2)
Figure 2:
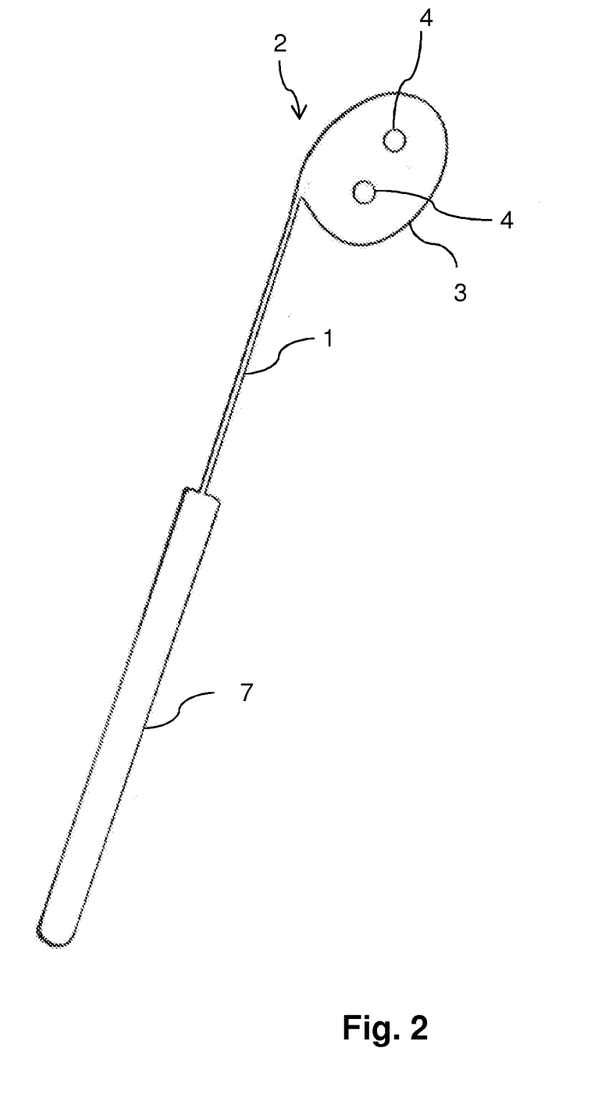

FIGS. 1 and 2 show an—implied—schematic representation of a device according to the invention for the patient-specific, individual anatomic placement of bore canals on the thigh and lower leg during anterior cruciate ligament reconstruction.

The device comprises a probe 1 to be inserted into the joint through an arthroscopy portal. A targeting head 2 is provided at the distal end of the probe. It holds an individually produced targeting template 3, which was generated on the basis of a 3D MRI or a 3D CT scan in accordance with the actual conditions of the respective patient and optimized in preparation of the production.

FIG. 1 specifically shows a device having a passage 4 for realizing the single bundle technique, while FIG. 2 shows an exemplary embodiment of the device according to the invention having two passages 4, namely for realizing the double bundle technique. Guide sleeves 5 can be provided instead of simple passages 4.

Figure 3:
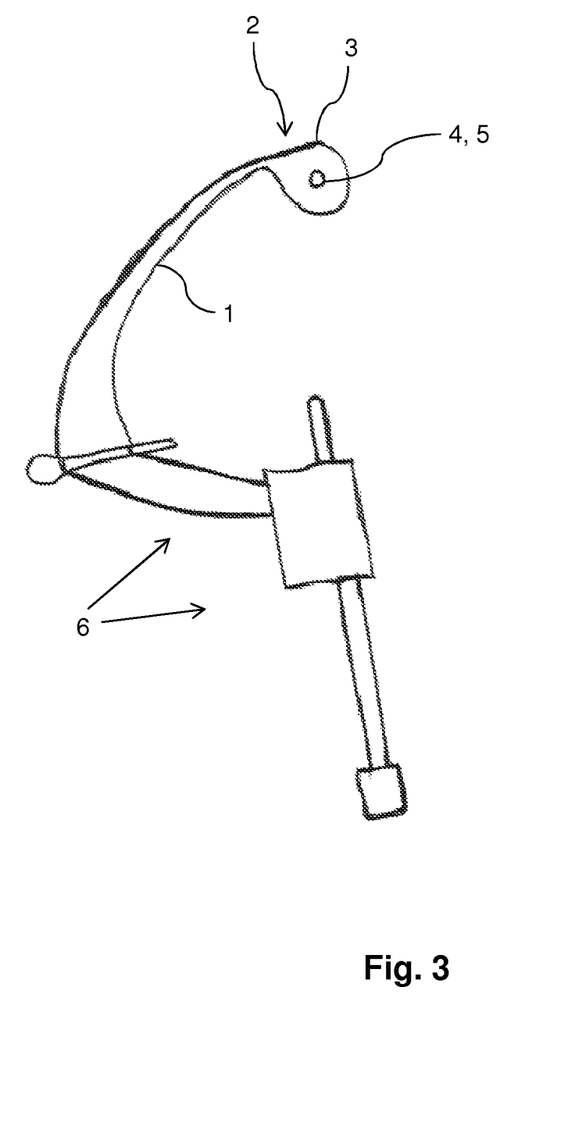
FIG. 3 shows a schematic representation of a further exemplary embodiment of a device according to the invention, comprising a probe with targeting head and individual targeting template and a fixation device for attaching the probe in the region of the cruciate ligament from outside of the incision.

FIG. 3 shows a further exemplary embodiment of a device according to the invention, wherein in it, the probe 1 with the targeting head 2 and the targeting template 3 is part of the fixation device 6. The fixation device 6 is used for positioning or attachment for example on the shinbone, while the probe 1 with the targeting head 2 and the targeting template 3 is inserted into the knee through a portal, where it is put on in an accurately fitting fashion.

The device according to the invention is equipped with a probe to be inserted into a joint through an arthroscopy portal. A targeting head is provided at the distal end of the probe. The targeting head comprises a targeting template, which has been produced individually using a 3D imaging method, in particular 3D magnetic resonance tomography or 3D computed tomography. Specifically, the targeting template is a negative imprint of the osseous surface contour in the region where the torn ligament attaches to the respective bone, in particular where the cruciate ligament attaches to the thigh or lower leg.

In other words, the device according to the invention is a customized anterior cruciate ligament targeting instrument for the patient-specific, individual anatomic placement of bore canals on the thigh and lower leg based on a 3D magnetic resonance image or a 3D computed tomography scan conducted before the surgery.

The targeting template comprises at least one passage for marking the bore canal to be produced on the bone, namely for the so-called single bundle technique. For the realization of the double bundle technique, the targeting template comprises two passages for marking two bore canals on the bone. From a design point of view, a handle grip for positioning is provided at the proximal end of the probe, such that a hand-held targeting device with an individual targeting head or with an individual targeting template is created in the fashion according to the invention.

As stated in the claims, the method according to the invention comprises the following procedure steps:

Conduct of a 3D MRI or a 3D CT scan of the injured joint and optionally the healthy joint, in particular the knee, to obtain 3D data;

Generation of a 3D computer model of the injured joint having the respective surface profile, in particular the respective surface profile of the individual attachment point of the cruciate ligament on the thigh and lower leg, using suitable software;

Creation of individual targeting templates, targeting heads and/or targeting devices.

The invention is based on the latest know-how used in cruciate ligament surgery, according to which a size-adapted, "customized" anterior cruciate ligament replacement is to be realized. In so doing, the major size differences between knee joints should be accounted for. Accordingly, smaller knee joints have a smaller attachment point of the cruciate ligament and vice versa. The size of the knee does not necessarily correlate with the size of a person. In any case, corresponding size differences between knees are currently not individually considered during the surgery. Said individual consideration can artfully be achieved on the basis of the device according to the invention, manufactured as stated in the method according to the invention.

While the cruciate ligament targeting devices for the creation of the bore canals on the thigh and shinbone as they are known from the practice fail to deliver distinct assistance with the placement of the bore canals and in addition fail to account for the individual size of the cruciate ligament insertion on the thigh and on the shinbone, the device according to the invention provides a customized cruciate ligament targeting instrument, which enables an individual reconstruction of the cruciate ligament.

The individually manufactured targeting template and optionally the entire targeting head including the targeting template can be exchanged on the instrument in an advantageous fashion.

According to certain of the independent claims, the probe with the targeting head and the targeting template is part of a fixation device for attaching the probe in the region of the cruciate ligament or can be combined with a corresponding fixation device. Said type of targeting device is inserted with the probe into the joint, for example through an arthroscopy portal, whereby part of the targeting device located outside the joint is applied and positioned accurately fitting for example on the shinbone.

At this point, it should be noted that the invention utilizes the individual adjustment of a targeting template or a targeting head, irrespective of the specific device and irrespective of the specific technique that is used. The individualization of the targeting template is relevant to account for the anatomical conditions.

The fixation device comprises at least one guide sleeve for defining the drill hole location and/or the drilling angle and/or the drilling diameter and/or for guiding wires, etc., namely for the purpose of the reconstruction. An optimal surgical instrument is thus created.

In light of the explanations provided above, it becomes clear that the device according to the invention makes it possible to provide two individually manufactured targeting templates and targeting devices for each patient, namely one each for the thigh and the lower leg. The production is based on a 3D magnetic resonance image or a 3D computed tomography image, whereby it is essentially possible to use any types of imaging methods. The device according to the invention helps ensure the correct individual anatomical placement of the bore canals on the thigh and lower leg during cruciate ligament reconstruction.

Taking into account the size of the attachment point of the cruciate ligament on the thigh and lower leg, an ideal size of the bore canals can be specified with the use of a so-called insertion table. The device according to the invention can then be manufactured for both the single bundle technique with one bore canal as well as for the double bundle technique with two bore canals, such that the reconstruction of the individual length/surface area of the attachment point of the cruciate ligament on the thigh and lower leg is ensured individually for each patient.

The device according to the invention with the individual targeting template is manufactured on the basis of the 3D magnetic resonance tomography or the 3D computed tomography image of the injured knee and—in a further advantageous fashion—also of the healthy knee, to allow a comparative optimization.

Suitable software is used to "produce" a digital 3D model of the injured knee in the computer model or to simulate a 3D model. Said model visualizes the osseous surface profile and the attachment points of the torn cruciate ligament on the thigh and lower leg. A 3D model of the healthy knee can be produced to illustrate the stumps of the cruciate ligaments, to facilitate a comparison for optimization purposes.

Two digital targeting templates for the thigh and lower leg can be produced based on the computer model, to help equip an individual targeting device accordingly. The targeting templates are ultimately negative imprints of the actual surface profile and accurately fit on the individual surface contour of the respective patient in the area of the attachment point of the cruciate ligament on the thigh and lower leg.

In addition, it is conceivable to use the individually designed targeting templates or targeting devices to conduct a simulation on the 3D computer model by means of suitable software, such that it is possible to review the digital templates on the complete targeting device prior to the actual manufacture of the targeting templates. In a particularly advantageous fashion, said controls can be conducted by the future surgeon by means of the 3D model, such as to allow him to review the function resulting from the optimization. Furthermore, the surgeon has the option of making corrections to the 3D model, namely to realize a further optimization.

In addition, it is conceivable that the localization of the bore canals, the drilling angles, the size of the bore canals as well as the technique to be conducted (single bundle or double bundle) are defined interactively, to the extent possible on the basis of data retrievable from a file, for example on the basis of data contained in an insertion table. Manual data input is likewise an option.

Following the optimization, the patient-specific targeting templates and optionally targeting devices for thighs and lower legs are manufactured on the basis of the optimized 3D model, preferably of metal or synthetic material. Any shape-giving methods can be used, wherein the manufacture is based on the optimized 3D data.

The targeting devices manufactured in this fashion can be placed accurately fitting onto the respective patient's osseous surface contour and adjusted there. During the surgery, the drills are applied by means of integrated guide sleeves for the creation of the bore canals or the Kirschner wires are threaded through the bore canals for the performance. Only then are the targeting devices removed from the thigh and lower leg.

It is basically conceivable that the individually manufactured targeting template or the individually manufactured targeting head can be mounted on commercially available targeting devices, wherein the targeting devices known from the practice for placement on the lower leg can consist of two parts and the targeting devices for the thigh can regularly consist of only one part.

The targeting template according to the invention and a complete targeting device are used in surgeries as follows:

The individual tibial targeting template (for the thigh) is mounted accurately fitting onto the osseous surface contour through an arthroscopy portal under arthroscopic view and adjusted there. The targeting template is retained from the outside with a grab handle. Then, the spaces of the bore holes can be used to mark the bore canals. Next, the templates are removed from the joint and holes are drilled in common fashion at the marked locations.

The individual tibial targeting device is likewise inserted into the joint through an arthroscopy portal. It is adjusted to the osseous surface profile of the lower leg in the region of the cruciate ligament under arthroscopic view. The part of the tibial targeting device located outside the joint is placed accurately fitting onto the shinbone. As a result, the drilling angle on the tibial head is defined quasi automatically. Based on the design of the targeting device, the desired bore canal diameter with the corresponding defined angle is drilled using either the traditional single bundle technique or the double bundle technique, on the basis of the guide sleeves assigned to the targeting head. Kirschner wires can then be inserted. Essentially, the specific technique is irrelevant, according to which either a single bore canal or two bore canals are produced.

The device according to the invention or the individually produced targeting device can likewise be used on the lower leg, both within the scope of a hand-held instrument as well as within the scope of a targeting device to be mounted from the outside.

The individual femoral targeting template (for the thigh) is placed accurately fitting onto the osseous surface contour through an arthroscopy portal under arthroscopic view and adjusted there. It is retained from the outside with a grab handle. The spaces of the bore holes can then be used for marking the bore canals. Next, the templates are removed from the joint and holes drilled in the common fashion at the marked locations.

The individual femoral targeting device is inserted into the femoral region of the cruciate ligament with the patient-specific imprint of the surface structure, i.e., with the patient-specific template, namely through an anteromedial or anterolateral arthroscopy portal. The instrument is put onto the osseous structures of the region of the cruciate ligament with its accurately fitting 3D imprint on the thigh in the region of the lateral wall of the intercondylar notch under arthroscopic view. In this case, the holes are drilled through an anteromedial portal.

Alternatively, the instrument or the targeting arm can be inserted through the anterolateral portal. So-called outside-in drilling from the lateral thigh is possible.

Based on the individual design of the targeting device, the holes are drilled analogous to one or two guide sleeves for the realization of the single bundle technique or the double bundle technique with a defined diameter of the bore canals. Kirschner wires can be inserted through the bore hole(s).

After the creation of the bore canals, the transplant is inserted and fastened in a traditional fashion, namely on the basis of an individual creation of the bore canals and in consideration of the patient-specific conditions.

Finally, explicit reference is made to the fact that the exemplary embodiments of the device according to the invention described above are used only for explanation of the claimed teaching, but the teaching is not restricted to the exemplary embodiments.

LIST OF REFERENCE NUMBERS

1 Probe
2 Targeting head
3 Targeting template
4 Passage
5 Guide sleeve
6 Fixation device
7 Grab handle

The invention claimed is:

1. A method for the manufacture of a device configured for the patient-specific, individual anatomic placement of bore canals when attaching artificial ligaments to the thigh or lower leg during anterior cruciate ligament reconstruction, said method comprising the following steps:
conducting at least one of a 3D MRI or a 3D CT scan of an injured joint and a healthy joint to obtain for each 3D data;
generating 3D computer models of the injured joint and the healthy joint, the 3D computer models having the respective surface profile of the individual attachment point of the cruciate ligament on the thigh and lower leg, using suitable software;
comparing the 3D computer model of the injured joint and the 3D computer model of the healthy joint;
optimizing the 3D data obtained based upon the comparison of the 3D computer model of the injured joint and the 3D computer model of the healthy joint; and
creating at least one of individual targeting templates (3), targeting heads (2), or targeting devices for provision at the distal end of a probe (1) of the device, the probe (1) being configured to be inserted into the injured joint through an arthroscopy portal, the targeting heads (2) comprising at least one targeting template (3), the targeting templates (3) being a negative imprint of the osseous surface contour in the attachment area of the torn cruciate ligament on the thigh or lower leg and comprising at least one passage (4) for marking the bore canal, wherein a grab handle (7) is provided at the proximal end of the probe (1) for holding and positioning the individual targeting templates (3), targeting heads (2), or targeting devices.

2. A method according to claim 1, wherein at least one of a 3D MRI or a 3D CT scan of the joint is conducted to obtain 3D data.

3. A method according to claim 1, wherein digital (virtual) targeting templates (3) are created based on the 3D data, said targeting templates being used for simulation on definable or digitally created (virtual) targeting heads (2) and targeting devices to achieve an optimal adjustment to the osseous surface contour in the attachment area of the cruciate ligament on the thigh and lower leg prior to the production of the targeting template (3) or targeting head (2) or targeting device, respectively.

4. A method according to claim 3, wherein corrections of the virtual targeting templates (3), targeting heads (2) and/or targeting devices can be made during or after the simulation.

5. A method according to claim 1, wherein the surface contour is adjusted in consideration of parameters that can be entered or selected from a file.

6. A method according to claim 3, wherein the surface contour is adjusted in consideration of the localization of the bore canal, the drilling angle, the size of the bore canal and the general technique (single bundle or double bundle).

7. A method according to claim 1, wherein the targeting templates, targeting head and/or targeting devices are made of metal or synthetic material, following the optimized adjustment based on the data resulting from the optimization.

8. A method for the manufacture of a device configured for the patient-specific, individual anatomic placement of bore canals when attaching artificial ligaments to the thigh or lower leg during anterior cruciate ligament reconstruction, said method comprising the following steps:
conducting at least one of a 3D MRI or a 3D CT scan of an injured joint and a healthy joint to obtain for each 3D data;
generating 3D computer models of the injured joint and the healthy joint, the 3D computer models having the respective surface profile of the individual attachment point of the cruciate ligament on the thigh and lower leg, using suitable software;
comparing the 3D computer model of the injured joint and the 3D computer model of the healthy joint;
optimizing the 3D data obtained based upon the comparison of the 3D computer model of the injured joint and the 3D computer model of the healthy joint; and
creating at least one of individual targeting templates (3), targeting heads (2), or targeting devices for provision at the distal end of a probe (1) of the device, the probe (1) being configured to be inserted into the injured joint through an arthroscopy portal, the targeting heads (2) comprising at least one targeting template (3), the targeting templates (3) being a negative imprint of the osseous surface contour in the attachment area of the torn cruciate ligament on the thigh or lower leg, wherein the probe (1) with at least one of the targeting head (2) or the targeting template (3) is either part of a fixation device (6) for attaching the probe (1) in the region of the cruciate ligament or can be combined with an analogous fixation device (6), and wherein the fixation device (6) comprises at least one guide sleeve (5) for at least one defining the drill hole location, defining the drilling angle, defining the drilling diameter, or for guiding wires.

9. A method according to claim 8, wherein digital (virtual) targeting templates (3) are created based on the 3D data, said targeting templates being used for simulation on definable or digitally created (virtual) targeting heads (2) and targeting devices to achieve an optimal adjustment to the osseous surface contour in the attachment area of the cruciate ligament on the thigh and lower leg prior to the production of the targeting template (3) or targeting head (2) or targeting device, respectively.

10. A method according to claim 9, wherein corrections of the virtual targeting templates (3), targeting heads (2) and/or targeting devices can be made during or after the simulation.

* * * * *